(12) United States Patent
Engel

(10) Patent No.: US 10,561,706 B2
(45) Date of Patent: Feb. 18, 2020

(54) ISOLATED POLYPEPTIDE AND COMPOSITIONS COMPRISING SAME

(71) Applicant: B. G. NEGEV TECHNOLOGIES AND APPLICATIONS LTD., AT BEN-GURION UNIVERSITY, Beer Sheva (IL)

(72) Inventor: Stanislav Engel, Beer Sheva (IL)

(73) Assignee: B. G. NEGEV TECHNOLOGIES AND APPLICATIONS, Beer Sheva (IL)

(*) Notice: Subject to any disclaimer, the term of this patent is extended or adjusted under 35 U.S.C. 154(b) by 0 days.

(21) Appl. No.: 16/067,080

(22) PCT Filed: Dec. 28, 2016

(86) PCT No.: PCT/IL2016/051393
§ 371 (c)(1),
(2) Date: Jun. 28, 2018

(87) PCT Pub. No.: WO2017/115367
PCT Pub. Date: Jul. 6, 2017

(65) Prior Publication Data
US 2019/0022179 A1  Jan. 24, 2019

Related U.S. Application Data

(60) Provisional application No. 62/271,470, filed on Dec. 28, 2015.

(51) Int. Cl.
| C07K 14/435 | (2006.01) |
| A61K 38/17 | (2006.01) |
| A61K 39/00 | (2006.01) |
| A61P 25/02 | (2006.01) |
| C07K 4/12 | (2006.01) |
| C07K 7/04 | (2006.01) |
| C07K 16/40 | (2006.01) |

(52) U.S. Cl.
CPC .......... *A61K 38/17* (2013.01); *A61K 39/0007* (2013.01); *A61P 25/02* (2018.01); *C07K 4/12* (2013.01); *C07K 7/04* (2013.01); *C07K 14/435* (2013.01); *C12Y 115/01001* (2013.01); *A61K 2039/6031* (2013.01); *A61K 2300/00* (2013.01); *C07K 16/40* (2013.01)

(58) Field of Classification Search
None
See application file for complete search history.

(56) References Cited

U.S. PATENT DOCUMENTS

| 3,791,932 A | 2/1974 | Schuurs et al. |
| 3,839,153 A | 10/1974 | Schuurs et al. |
| 3,850,578 A | 11/1974 | Mcconnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,816,567 A | 3/1989 | Cabilly et al. |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 8,709,422 B2 | 4/2014 | Cashman et al. |
| 9,109,037 B2 | 8/2015 | Ambrosino et al. |
| 2012/0028266 A1 | 2/2012 | Wells et al. |
| 2014/0044722 A1* | 2/2014 | Ambrosino ............ C07K 16/40 424/139.1 |

FOREIGN PATENT DOCUMENTS

WO  2007098607 A1  9/2007

OTHER PUBLICATIONS

Benatar, M., Lost in translation: Treatment trials in the SOD1 mouse and in human ALS, 2007, Neurobiology of Disease 26: 1-13 (Year: 2007).*
DiBernardo et al., Translating preclinical insights into effective human trials in ALS, 2006, Biochimica et Biophysica Acta 1762: 1139-1149 (Year: 2006).*
R. B. Merrifield, "Solid Phase Peptide Synthesis. I. The Synthesis of a Tetrapeptide", Journal of the American Chemical Society, 1963, pp. 2149-2154, vol. 85, No. 14.
Siegmund Reissmanna, "Cell penetration: scope and limitations by the application of cell-penetrating peptides", Journal of Peptide Science, Oct. 2014, pp. 760-784, vol. 20 No. 10.
G.T. Köhler et al., "Continuous culture of fused cells secreting antibody of predefined specificity", Nature Publishing Group, Aug. 7, 1975, pp. 495-497, vol. 256.
Clackson T et al. "Making antibody fragments using phage display libraries", Nature, Aug. 15, 1991, pp. 624-628, vol. 352, No. 6336.
Marks JD et al., "By-passing immunization. Human antibodies from V-gene libraries displayed on phage", Journal of Molecular Biology, Dec. 5, 1991, pp. 581-597, vol. 222, No. 3.
Danuta Kozbor et al., "The production of monoclonal antibodies from human lymphocytes", Immunology Today, Mar. 1983, pp. 72-79, vol. 4, No. 3.

(Continued)

Primary Examiner — John D Ulm
(74) Attorney, Agent, or Firm — The Roy Gross Law Firm, LLC; Roy Gross

(57) ABSTRACT

The present invention provides a composition and method for treating, delaying the onset, delaying progression of, reducing the incidence of or reducing the severity of amyotrophic lateral sclerosis in a subject. The composition a peptide derived from SOD1 which can be used to inhibit formation of SOD1 amyloid-like aggregates or for production of anti-SOD1 antibodies.

18 Claims, 8 Drawing Sheets

Specification includes a Sequence Listing.

(56) References Cited

OTHER PUBLICATIONS

Roman Osman et al., "The Role of Protein "Stability Patches" in Molecular Recognition: A Case Study of the Human Growth Hormone-Receptor Complex", Journal of Computational Chemistry, Dec. 21, 2015, pp. 913-919, vol. 37.

Banerjee. et al, "Superoxide Dismutase 1 (SOD1)-Derived Peptide Inhibits Amyloid Aggregation of Familial Amyotrophic Lateral Sclerosis SOD1 Mutants", ACS Chemical Neuroscience, Aug. 19, 2016, pp. 1595-1606, vol. 7, No. 11, May 2009.

International Search Report PCT/IL2016/051393 completed Apr. 19, 2017; dated Apr. 20, 2017 8 pages.

Written Opinion of the International Searching Authority PCT/IL2016/051393 dated Apr. 20, 2017 6 pages.

Daryl A Bosco et al., "Wild-type and mutant SOD1 share an aberrant conformation and a common pathogenic pathway in ALS." Nature Neuroscience. Nov. 2010, pp. 1396-1403, vol. 13 No. 11.

Broering TJ et al, "Identification of human monoclonal antibodies specific for human SOD1 recognizing distinct epitopes and forms of SOD1", PLOS One, Apr. 2013, vol. 8 Issue 4, e61210.

* cited by examiner

MATKAVCVLKGDGPVQGIINFEQKESNGPVKVWGSIKGLTEGLHGFHVHEFGDNTAGCTSAGPHF

NPLSRKHGGPKDEERHVGDLGNVTA|DKDGVADVSIEDSVI|SLGDH|CI|GRTLVVHEKADD|LGK
                            SE-11               SE-12
                         (SEQ ID NO: 6)      (SEQ ID NO: 7)
GGNEESTKTGNAGSRLACGVIGIAQ (SEQ ID NO: 3)

Figure 1A

SE-1) ATKAVCVLKGDGPVQGIINF (SEQ ID NO: 15)   SE-8)  HGGPKDEERHVGDLGNVTAD (SEQ ID NO: 22)
SE-2) VCVLKGDGPVQGIINFEQKE (SEQ ID NO: 16)   SE-9)  DLGNVTADKDGVADVSIEDS (SEQ ID NO: 23)
SE-3) NGPVKVWGSIKGLTEGLHGF (SEQ ID NO: 17)   SE-10) NVTADKDGVADVSIEDSVIS (SEQ ID NO: 24)
SE-4) KVWGSIKGLTEGLHGFHVHE (SEQ ID NO: 18)   SE-11) DKDGVADVSIEDSVISLSGD (SEQ ID NO: 6)
SE-5) SIKGLTEGLHGFHVHEFGDN (SEQ ID NO: 19)   SE-12) LSGDHCIIGRTLVVHEKADD (SEQ ID NO: 7)
SE-6) AGPHFNPLSRKHGGPKDEER (SEQ ID NO: 20)   SE-13) STKTGNAGSRLACGVIGIAQ (SEQ ID NO: 25)
SE-7) FNPLSRKHGGPKDEERHVGD (SEQ ID NO: 21)   SE-14) HEKADDLGKGGNEESTKTGN (SEQ ID NO: 26)

Figure 1B

SEQUENCE LISTING

<160> NUMBER OF SEQ ID NOS: 26

<210> SEQ ID NO 1
<211> LENGTH: 48

```
<212> TYPE: PRT
<213> ORGANISM: Homo sapiens

<400> SEQUENCE: 1

Leu Ser Gly Asp His Cys Ile Ile Gly Arg Thr Leu Val Val His Glu
1               5                   10                  15

Lys Ala Asp Asp Leu Gly Lys Gly Gly Asn Glu Glu Ser Thr Lys Thr
                20                  25                  30

Gly Asn Ala Gly Ser Arg Leu Ala Cys Gly Val Ile Gly Ile Ala Gln
            35                  40                  45

<210> SEQ ID NO 2
<211> LENGTH: 6
<212> TYPE: PRT
<213> ORGANISM: Homo sapiens

<400> SEQUENCE: 2

Leu Ser Gly Asp His Cys
1               5

<210> SEQ ID NO 3
<211> LENGTH: 154
<212> TYPE: PRT
<213> ORGANISM: Homo sapiens

<400> SEQUENCE: 3

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
        130                 135                 140

Leu Ala Cys Gly Val Ile Gly Ile Ala Gln
145                 150

<210> SEQ ID NO 4
<211> LENGTH: 7
<212> TYPE: PRT
<213> ORGANISM: Synthetic sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 4

Leu Ser Gly Asp His Cys Xaa
1               5
```

```
<210> SEQ ID NO 5
<211> LENGTH: 7
<212> TYPE: PRT
<213> ORGANISM: Synthetic sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 5

Xaa Leu Ser Gly Asp His Xaa
1               5

<210> SEQ ID NO 6
<211> LENGTH: 20
<212> TYPE: PRT
<213> ORGANISM: Homo sapiens

<400> SEQUENCE: 6

Asp Lys Asp Gly Val Ala Asp Val Ser Ile Glu Asp Ser Val Ile Ser
1               5                   10                  15

Leu Ser Gly Asp
            20

<210> SEQ ID NO 7
<211> LENGTH: 20
<212> TYPE: PRT
<213> ORGANISM: Homo sapiens

<400> SEQUENCE: 7

Leu Ser Gly Asp His Cys Ile Ile Gly Arg Thr Leu Val Val His Glu
1               5                   10                  15

Lys Ala Asp Asp
            20

<210> SEQ ID NO 8
<211> LENGTH: 28
<212> TYPE: PRT
<213> ORGANISM: Homo sapiens

<400> SEQUENCE: 8

Ser Ile Glu Asp Ser Val Ile Ser Leu Ser Gly Asp His Cys Ile Ile
1               5                   10                  15

Gly Arg Thr Leu Val Val His Glu Lys Ala Asp Asp
            20                  25

<210> SEQ ID NO 9
<211> LENGTH: 14
<212> TYPE: PRT
<213> ORGANISM: Homo sapiens

<400> SEQUENCE: 9

Ile Ile Gly Arg Thr Leu Val Val His Glu Lys Ala Asp Asp
1               5                   10

<210> SEQ ID NO 10
<211> LENGTH: 14
<212> TYPE: PRT
<213> ORGANISM: Homo sapiens

<400> SEQUENCE: 10
```

Asp Lys Asp Gly Val Ala Asp Val Ser Ile Glu Asp Ser Val
1               5                   10

<210> SEQ ID NO 11
<211> LENGTH: 17
<212> TYPE: PRT
<213> ORGANISM: Homo sapiens

<400> SEQUENCE: 11

Glu Asp Ser Val Ile Ser Leu Ser Gly Asp His Cys Ile Ile Gly Arg
1               5                   10                  15

Thr

<210> SEQ ID NO 12
<211> LENGTH: 18
<212> TYPE: PRT
<213> ORGANISM: Homo sapiens

<400> SEQUENCE: 12

Leu Ser Gly Asp His Cys Ile Ile Gly Arg Thr Leu Val Val His Glu
1               5                   10                  15

Lys Ala

<210> SEQ ID NO 13
<211> LENGTH: 15
<212> TYPE: PRT
<213> ORGANISM: Homo sapiens

<400> SEQUENCE: 13

Leu Ser Gly Asp His Cys Ile Ile Gly Arg Thr Leu Val Val His
1               5                   10                  15

<210> SEQ ID NO 14
<211> LENGTH: 11
<212> TYPE: PRT
<213> ORGANISM: Homo sapiens

<400> SEQUENCE: 14

Leu Ser Gly Asp His Cys Ile Ile Gly Arg Thr
1               5                   10

<210> SEQ ID NO 15
<211> LENGTH: 20
<212> TYPE: PRT
<213> ORGANISM: Homo sapiens

<400> SEQUENCE: 15

Ala Thr Lys Ala Val Cys Val Leu Lys Gly Asp Gly Pro Val Gln Gly
1               5                   10                  15

Ile Ile Asn Phe
            20

<210> SEQ ID NO 16
<211> LENGTH: 20
<212> TYPE: PRT
<213> ORGANISM: Homo sapiens

<400> SEQUENCE: 16

Val Cys Val Leu Lys Gly Asp Gly Pro Val Gln Gly Ile Ile Asn Phe
1               5                   10                  15

Glu Gln Lys Glu
            20

```
<210> SEQ ID NO 17
<211> LENGTH: 20
<212> TYPE: PRT
<213> ORGANISM: Homo sapiens

<400> SEQUENCE: 17

Asn Gly Pro Val Lys Val Trp Gly Ser Ile Lys Gly Leu Thr Glu Gly
1               5                   10                  15

Leu His Gly Phe
            20

<210> SEQ ID NO 18
<211> LENGTH: 20
<212> TYPE: PRT
<213> ORGANISM: Homo sapiens

<400> SEQUENCE: 18

Ser Ile Lys Gly Leu Thr Glu Gly Leu His Gly Phe His Val His Glu
1               5                   10                  15

Phe Gly Asp Asn
            20

<210> SEQ ID NO 19
<211> LENGTH: 20
<212> TYPE: PRT
<213> ORGANISM: Homo sapiens

<400> SEQUENCE: 19

Ala Gly Pro His Phe Asn Pro Leu Ser Arg Lys His Gly Gly Pro Lys
1               5                   10                  15

Asp Glu Glu Arg
            20

<210> SEQ ID NO 20
<211> LENGTH: 20
<212> TYPE: PRT
<213> ORGANISM: Homo sapiens

<400> SEQUENCE: 20

Phe Asn Pro Leu Ser Arg Lys His Gly Gly Pro Lys Asp Glu Glu Arg
1               5                   10                  15

His Val Gly Asp
            20

<210> SEQ ID NO 21
<211> LENGTH: 20
<212> TYPE: PRT
<213> ORGANISM: Homo sapiens

<400> SEQUENCE: 21

His Gly Gly Pro Lys Asp Glu Glu Arg His Val Gly Asp Leu Gly Asn
1               5                   10                  15

Val Thr Ala Asp
            20

<210> SEQ ID NO 22
<211> LENGTH: 20
<212> TYPE: PRT
<213> ORGANISM: Homo sapiens

<400> SEQUENCE: 22

Asp Leu Gly Asn Val Thr Ala Asp Lys Asp Gly Val Ala Asp Val Ser
```

```
1               5                  10                  15

Ile Glu Asp Ser
            20

<210> SEQ ID NO 23
<211> LENGTH: 20
<212> TYPE: PRT
<213> ORGANISM: Homo sapiens

<400> SEQUENCE: 23

Asn Val Thr Ala Asp Lys Asp Gly Val Ala Asp Val Ser Ile Glu Asp
1               5                   10                  15

Ser Val Ile Ser
            20

<210> SEQ ID NO 24
<211> LENGTH: 20
<212> TYPE: PRT
<213> ORGANISM: Homo sapiens

<400> SEQUENCE: 24

Ser Thr Lys Thr Gly Asn Ala Gly Ser Arg Leu Ala Cys Gly Val Ile
1               5                   10                  15

Gly Ile Ala Gln
            20

<210> SEQ ID NO 25
<211> LENGTH: 20
<212> TYPE: PRT
<213> ORGANISM: Homo sapiens

<400> SEQUENCE: 25

His Glu Lys Ala Asp Asp Leu Gly Lys Gly Gly Asn Glu Glu Ser Thr
1               5                   10                  15

Lys Thr Gly Asn
            20

<210> SEQ ID NO 26
<211> LENGTH: 20
<212> TYPE: PRT
<213> ORGANISM: Homo sapiens

<400> SEQUENCE: 26

Lys Val Trp Gly Ser Ile Lys Gly Leu Thr Glu Gly Leu His Gly Phe
1               5                   10                  15

His Val His Glu
            20
```

ISOLATED POLYPEPTIDE AND COMPOSITIONS COMPRISING SAME

CROSS-REFERENCE TO RELATED APPLICATIONS

This application is a National Phase of PCT Patent Application No. PCT/IL2016/051393 having International filing date of Dec. 28, 2016, which claims the benefit of priority from U.S. Patent Application No. 62/271,470 filed on Dec. 28, 2015 entitled "COMPOSITION AND METHOD FOR TREATING AMYOTROPHIC LATERAL SCLEROSIS." The contents of the above applications are all incorporated herein by reference as if fully set forth herein in their entirety.

FIELD OF INVENTION

The present invention is directed to peptides derived from SOD1, compositions comprising same and methods of use thereof including but not limited to methods for inhibiting formation of SOD1 amyloid-like aggregates, for producing anti-SOD1 antibodies and for treating amyotrophic lateral sclerosis (ALS).

BACKGROUND OF THE INVENTION

Protein aggregation and misfolding diseases, or proteopathies, constitute a broad range of debilitating diseases such as Alzheimer's disease, Parkinson's disease, cystic fibrosis, prion disease, type 2 diabetes, amyloidosis, and amyotrophic lateral sclerosis (ALS). Mutations or environmental stresses can cause proteins to assume abnormal structures (i.e., misfolding) that result in either the loss of the protein's original function or in the gain of a new, noxious function. At the molecular level, the progression of a proteopathy is frequently characterized by the sequential structural transformation of the protein involved that eventually results in protein aggregation, but the identity of the intermediate species responsible for the protein's toxicity is unknown in most cases.

ALS proteopathy is a rapidly progressing neurodegenerative disease with a varied etiology characterized by the gradual degeneration and death of motor neurons. Currently, there are no effective therapeutic agents for ALS, and there is only one FDA-approved drug for its treatment, riluzole, which only delays the need for a ventilator and may extend life by up to three months.

Approximately 20% of familial ALS cases result from mutations in the gene that encodes the enzyme copper-zinc superoxide dismutase 1 (SOD1), a ubiquitous 32 kDa homodimeric protein critical to cellular defense against reactive oxygen species. To date, over 150 mutations in SOD1 have been identified and described as causing ALS in a dominant fashion (FALS mutations), but their distribution throughout the SOD1 sequence exhibits no apparent pattern. In addition, it has been suggested that a significant fraction of sporadic ALS cases is caused by the exposure of wild type SOD1 (SOD1WT) to cellular stress, which may be cell- or tissue-specific. Phenotypically, SOD1-related ALS is universally manifested by SOD1 misfolding and aggregation, and the pathogenesis is attributed to novel noxious function(s) acquired by SOD1 upon misfolding. Downstream physiological effects of gain-of-function SOD1 toxicity include, among others, impaired mitochondrial metabolism, axonal degeneration, axonal transport failure, excitotoxicity, proteasomal disruption, and endoplasmic reticulum stress. The nature of the toxic SOD1 species and the mechanism of their toxicity remain obscure.

Disease-causing mutations may induce SOD1 misfolding by promoting SOD1 demetallation (i.e., formation of apo-SOD1) and the reduction of the stabilizing intra-subunit disulfide bond, thereby reducing the stability of SOD1 monomers or destabilizing the dimer interface. Mutations could also interfere with SOD1 binding to the copper chaperone for SOD1 (CCS), which normally recognizes newly synthesized SOD1 and activates it by facilitating the insertion of catalytic copper and the oxidation of the disulfide bond. With its progressively decreased global stability, misfolded SOD1 eventually precipitates to form amyloid-like aggregates. Soluble monomers and low-molecular weight oligomers formed along the aggregation pathway are particularly attractive candidate noxious species.

The acquired ability of misfolded SOD1 to form aberrant interactions with a variety of cellular proteins and interfere with their normal functions constitutes a potential pathogenic mechanism of SOD1-related ALS. Unlike SOD1WT, misfolded SOD1 mutants (SODMUT) interact with proteins such as HoxB2, a homeodomain-containing transcription factor, cytosolic malate dehydrogenase (MDH1), the voltage-dependent anion channel (VDAC1), Bcl-2, brain calcineurin, the axonal dynein complex, and derlin-1, among others. This ability to interact with structurally diverse proteins is a feature of proteins whose surfaces are characterized by the presence of conformationally adaptive interaction hot spot(s). Indeed, the 'gain-of-interaction' of misfolded SOD1 may indicate that upon misfolding, certain elements of the SOD1 surface acquire functional characteristics typical of energetic hot spots. Due to the high abundance of SOD1 (~1% of total human proteins) and its ubiquity (extracellular, cytoplasmic, nuclear, intra-mitochondrial), such a 'hot spot on the loose' scenario may inflict substantial cell damage by perturbing proper PPI homeostasis. Selective damage to motor neurons in ALS may be caused by misfolded SOD1 interfering with the activity of protein(s) predominantly expressed in these cells or playing a vital role in cell homeostasis.

There is an unmet need for novel therapies for the treatment of ALS. Inhibition of aggregation of misfolded SOD1 may be valuable for the treatment and prevention of ALS.

SUMMARY OF THE INVENTION

The present invention provides peptides derived from SOD1 and compositions comprising same. The present invention further provides methods for treating, delaying the onset, delaying progression of, reducing the incidence of or reducing the severity of amyotrophic lateral sclerosis (ALS).

In one aspect, the present invention provides an isolated polypeptide of less than 50 amino acids, said polypeptide comprises the amino acid sequence as set forth in SEQ ID NO: 2 (LSGDHC).

In some embodiments, the isolated polypeptide of the present invention comprises the amino acid sequence as set forth in SEQ ID NO: 4 (LSGDHCX$_1$), wherein X$_1$ represents an amino acid sequence of 1 to 15 amino acid residues, contiguous thereto.

In some embodiments, the isolated polypeptide of the present invention comprises or consists of an amino acid sequence as set forth in SEQ ID NO: 7 (LSGDHCIIGRTLVVHEKADD) or an amino acid sequence having at least 95% homology to SEQ ID NO: 7.

In some embodiments, the isolated polypeptide of the present invention comprises the amino acid sequence as set forth in SEQ ID NO: 5 ($X_2LSGDHCX_3$), wherein $X_2$ represents between 1 to 15 amino acid residues preceding thereto and $X_3$ represents between 1 to 15 amino acid residues contiguous thereto In some embodiments, the isolated polypeptide of the present invention comprises or consists of an amino acid sequence as set forth in SEQ ID NO: 11 (EDSVISLSGD-HCIIGRT) or an amino acid sequence having at least 95% homology to SEQ ID NO: 11.

In some embodiments, the isolated polypeptide of the present invention has a length of less than 40 amino acids. In some embodiments, the isolated polypeptide of the present invention has a length of less than 30 amino acids. In some embodiments, the isolated polypeptide of the present invention has a length of less than 20 amino acids.

In some embodiments, the isolated polypeptide of the present invention further comprises a cell-penetrating moiety. In some embodiments, the cell-penetrating moiety is a cell-penetrating peptide (CPP). In some embodiments, said CPP is linked to the N-terminus or C-terminus of the polypeptide of the invention. In some embodiments, said polypeptide of the invention and said CPP are linked by a peptide bond.

In another aspect, there is provided a pharmaceutical composition comprising as an active ingredient a pharmaceutically acceptable amount of the polypeptide of the present invention and a pharmaceutically acceptable carrier.

In some embodiments, the pharmaceutical composition is for use in inhibiting formation of SOD1 amyloid-like aggregates in a subject in need thereof.

In some embodiments, the pharmaceutical composition comprises a polypeptide having the amino acid sequence of SEQ ID NO: 1 (LSGDHCIIGRTLVVHEKADDLGKG-GNEESTKTGNAGSRLACGVIGIAQ).

In some embodiments, the composition comprises a polypeptide having the amino acid sequence of SEQ ID NO: 11.

In some embodiments, the polypeptides of the invention, or pharmaceutical compositions comprising same are useful for production of anti-SOD1 antibodies. In another embodiment, said antibodies are monoclonal antibodies. In some embodiments, the composition further comprises an adjuvant.

In another aspect, there is provided a method for treating a subject afflicted with ALS, the method comprises administering to said subject an effective amount of the pharmaceutical composition of the present invention, thereby treating a subject afflicted with ALS.

In another aspect, there is provided a pharmaceutical composition comprising as an active ingredient a pharmaceutically acceptable amount of an isolated polypeptide as described herein, and a pharmaceutically acceptable carrier, for use in treating, ameliorating or preventing ALS in a subject in need thereof.

In another aspect, there is provided a kit comprising a pharmaceutical composition comprising as an active ingredient a pharmaceutically acceptable amount of an isolated polypeptide as described herein, and a pharmaceutically acceptable carrier, for use in treating, ameliorating or preventing ALS in a subject in need thereof.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 1A-1B present the design of peptides for the SOD1 binding assay. FIG. 1A shows the distribution of 'stability patch' residues along the SOD1 primary structure. Stability patch residues are shaded in grey. FIG. 1B is a list of the 20-mer peptides that were designed to cover SOD1 areas enriched in stability patch residues. The sequences of peptides SE-11 (SEQ ID NO: 6; DKDGVADVSIEDS-VISLSGD) and SE-12 (SEQ ID NO: 7; LSGDHCIIGRTLV-VHEKADD) are indicated.

FIG. 2A is a picture showing SOD1$^{WT}$ and SOD1G93A proteins expressed and purified from E. coli that were assessed for their enzymatic activity with an in-gel activity assay;

FIG. 2B are graphs showing SOD and SOD proteins that were assessed structurally to determine their oligomeric state using size-exclusion chromatography as described in the methods section.

FIG. 4A are TEM images of SOD1$^{G93A}$ solution (50 mM) after 64 h incubation at 37° C. with continuous shaking. SOD1$^{G93A}$ was incubated alone (i-iii); in the presence of SE-11 (SEQ ID NO: 6) at a 1:0.2 (SOD1$^{G93}$A: SE-11 (SEQ ID NO: 6)) molar ratio (iv-vi); in the presence of SE-11 (SEQ ID NO: 6) at a 1:12 molar ratio (vii-ix); or in the presence of SE-12 (SEQ ID NO: 7) at 1:12 molar ratio (x-xii). FIG. 4B are TEM images of similar experiments as in FIG. 4A showing peptides SE-17 (SEQ ID NO: 8; SIEDSVISLSGDHCIIGRTLV-VHEKADD), SE-19 (SEQ ID NO: 9; IIGRTLV-VHEKADD), SE-20 (SEQ ID NO: 10; DKDGVAD-VSIEDSV) and SE-21 (SEQ ID NO: 11;

EDSVISLSGDHCIIGRT) can affect the morphology of the aggregates in a different manner (as described in Example 3).

Figure 5:
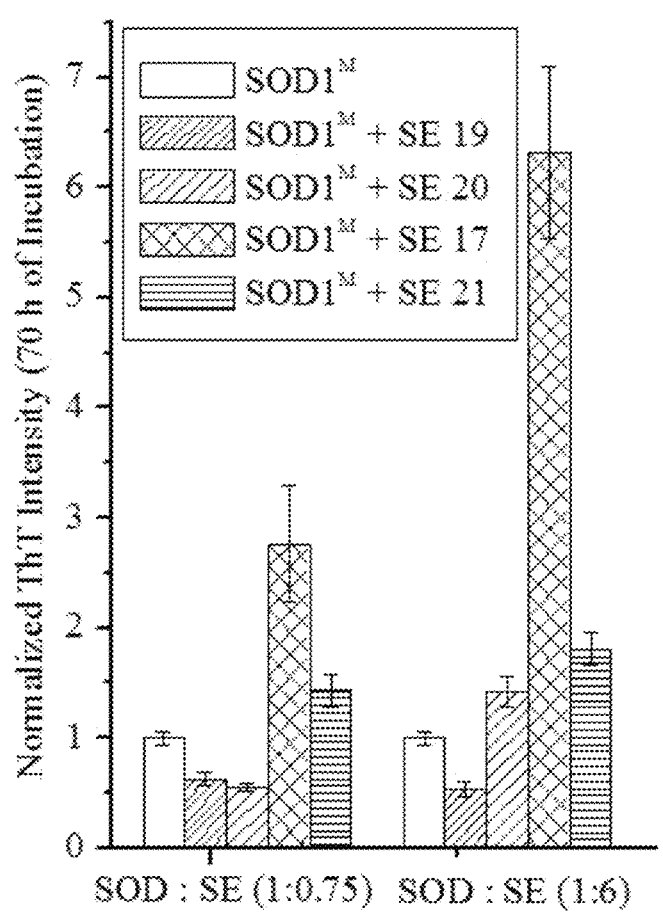

FIG. 5 is a bar graph showing the effect of SE-11 (SEQ ID NO: 8), SE-19 (SEQ ID NO: 9), SE-20 (SEQ ID NO: 10) and SE-21 (SEQ ID NO: 11) on SOD1$^{G93A}$ aggregation. ThT fluorescence at 64 h incubation at 37° C. with continuous shaking for: SOD1$^{G93A}$ alone and in the presence of each of the peptides. The values are normalized to the maximal ThT intensity obtained with SOD1$^{G93A}$ alone. All results are expressed as the mean±S.D. of assays performed in triplicate in a representative experiment. SOD1M designates SOD1$^{G93}$A.

Figure 6A:
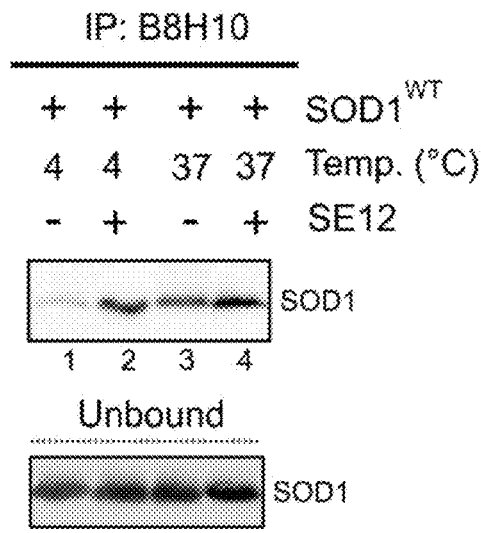
Figure 6C:
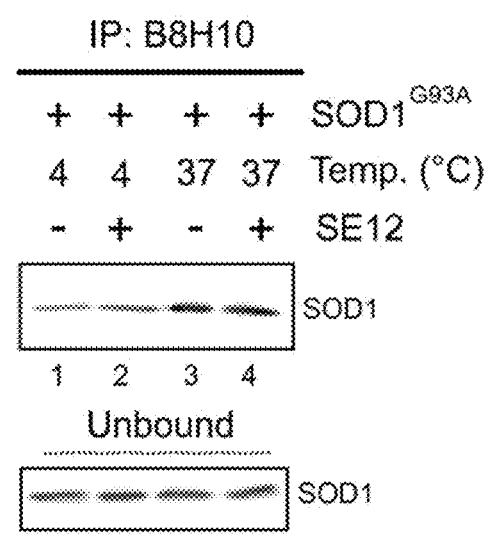
Figure 6B:
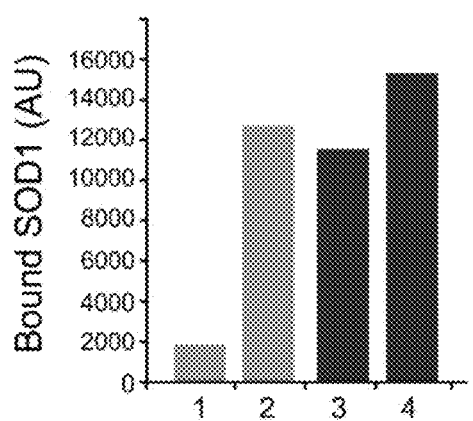
Figure 6D:
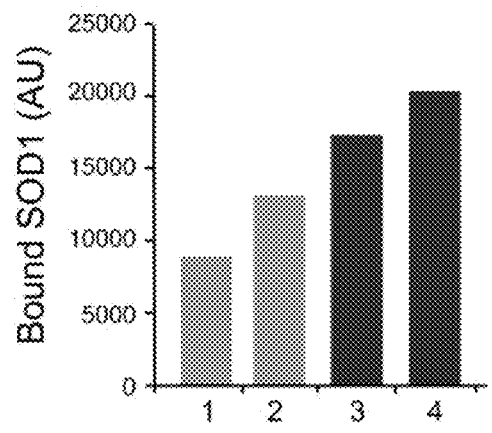

FIGS. 6A-6D are graphs showing that peptide SE-12 (SEQ ID NO: 7) induces SOD1 misfolding. A total of 50 mM of purified SOD1$^{WT}$ (FIGS. 6A-6B) or SOD1G93A (FIG. 6C-6D) was incubated in the presence of SE-12 (SEQ ID NO: 7) (600 mM) for 3 h at 4 or 37° C., followed by IP using the B8H10 monoclonal antibody specifically recognizing misfolded SOD1. The immunoprecipitated and unbound fractions were analyzed by Western blotting using anti-SOD1 antibody. The intensity of the bands corresponding to misfolded SOD1 (FIGS. 6A, 6C) was analyzed using ImageJ software (FIGS. 6B, 6D). The analysis of the unbound species demonstrates that a similar amount of SOD1 protein was present in the samples. The figure shows the data for a representative experiment of three similar independent experiments.

DETAILED DESCRIPTION OF THE INVENTION

The present invention provides, in some embodiments, peptides derived from SOD1, and compositions comprising same. The present invention further provides methods for treating or inhibiting the progress of amyotrophic lateral sclerosis (ALS) in a subject in need thereof.

The present invention is based, in part, on the surprising finding that specific peptides derived from SOD1 prevent the formation of amyloid-like aggregates of SOD1, and particularly of mutated and/or misfolded SOD1 linked to ALS formation.

According to some embodiments, the present invention provides an isolated peptide having a length of between 6 to 50 amino acids, said peptide comprises an amino acid sequence as set forth in SEQ ID NO: 2 (LSGDHC).

In another embodiment, said peptide comprising the amino acid sequence of SEQ ID NO: 2 has a length of between 1-20 amino acids, said peptide or derivative or fragment has at least 70%, at least 75%, at least 80%, at least 85%, at least 90%, at least 95% or at least 98% homology to a corresponding region in SEQ ID NO: 3.

In another embodiment, said peptide or derivative or fragment has a length of between 20-30 amino acids, said peptide or derivative or fragment has at least 70%, at least 75%, at least 80%, at least 85%, at least 90%, at least 95% or at least 98% homology to the amino acid sequence of SOD1 as set forth in of SEQ ID NO: 7.

In another embodiment, said peptide or derivative or fragment has a length of between 30-40 amino acids, said peptide or derivative or fragment has at least 70%, at least 75%, at least 80%, at least 85%, at least 90%, at least 95% or at least 98% homology to the amino acid sequence of SOD1 as set forth in of SEQ ID NO: 7.

In another embodiment, said peptide or derivative or fragment has a length of between 40-50 amino acids, said peptide or derivative or fragment has at least 70%, at least 75%, at least 80%, at least 85%, at least 90%, at least 95% or at least 98% homology to the amino acid sequence of SOD1 as set forth in of SEQ ID NO: 7.

According to another embodiment, the peptide of the present invention has a length of between 7 to 50 amino acids having the amino acid sequence set forth in SEQ ID NO: 4 (LSGDHCX$_1$), wherein X$_1$ represents between 1 to 44 amino acid residues contiguous to SEQ ID NO: 2.

By using the term "contiguous" such as in "amino acid residues contiguous" it is meant that the amino acids are linked to the defined peptide by a peptide bond thereby generating a single polypeptide chain. In some embodiments, the polypeptide of the present invention has SEQ ID NO: 2 at the proximal N-terminus and the amino acids defined as X$_1$ at the proximal C-terminus.

In another embodiment, X$_1$ comprises between 1-44 amino acid residues having at least 80% homology, at least 90% homology, at least 95% homology or at least 98% homology to SEQ ID NO: 1.

In some embodiments, the isolated polypeptide of the present invention comprises or consists of an amino acid sequence as set forth in SEQ ID NO: 7 (LSGDHCIIGRTLVVHEKADD) or a peptide having at least 95% homology to SEQ ID NO: 7.

In some embodiments, the isolated polypeptide of the present invention comprises the amino acid sequence as set forth in SEQ ID NO: 5 (X$_2$LSGDHCX$_3$), Wherein X$_2$ represents between 1 to 15 amino acid residues preceding thereto and X$_3$ represents between 1 to 15 amino acid residues contiguous thereto.

By using the term "amino acid residues preceding" it is meant that the amino acids are linked to a defined peptide by a peptide bond thereby generating a single polypeptide chain in which the sequence starts with the preceding sequence and continues with additional amino acids. In some embodiments, the peptide has the amino acids described as X$_2$ at the proximal N-terminus of the polypeptide and the amino acid sequence of SEQ ID NO: 2 as the proximal C-terminus. In some embodiments, the peptide has the amino acids described as X$_2$ at the proximal N-terminus, the amino acid sequence of SEQ ID NO: 2 as a middle portion and the amino acids described as X$_3$ at the proximal C-terminus.

In another embodiment, said peptide has a length of no more than 50 amino acids, no more than 49 amino acids, no more than 48 amino acids, no more than 47 amino acids, no more than 46, no more than 45 amino acids, no more than 44 amino acids, no more than 43 amino acids, no more than 42 amino acids, no more than 41, no more than 40 amino acids, no more than 39 amino acids, no more than 38 amino acids, no more than 37 amino acids, no more than 36, no more than 35 amino acids, no more than 34 amino acids, no more than 33 amino acids, no more than 32 amino acids, no more than 31 amino acids, no more than 30 amino acids, no more than 29 amino acids, no more than 28 amino acids, no more than 27 amino acids, no more than 26 amino acids, no more than 25 amino acids, no more than 24 amino acids, no more than 23 amino acids, no more than 22 amino acids, no more than 21 amino acids, or no more than 20 amino acids. Each possibility represents a spate embodiment of the present invention.

According to some embodiments, the present invention provides an isolated peptide having a length of 20 amino acids comprising an amino acid sequence as set forth SEQ ID NO: 7 (LSGDHCIIGRTLVVHEKADD). In another embodiment, the peptide of the present invention is a peptide having a length of 19, 18, 17, 16, 15, 14, 13, 12, 11, 10, 9, 8, 7 or 6 amino acids, wherein said peptide comprises the amino acid sequence as set forth SEQ ID NO: 2 at the proximal N-terminus.

In another embodiment, the present invention provides an isolated peptide having the amino acid sequence as set forth in SEQ ID NO: 12 (LSGDHCIIGRTLVVHEKA). In another embodiment, the present invention provides an isolated peptide having the amino acid sequence as set forth in SEQ ID NO: 13 (LSGDHCIIGRTLVVH). In another embodiment, the present invention provides an isolated peptide having the amino acid sequence as set forth in SEQ ID NO: 14 (LSGDHCIIGRT). In another embodiment, the present invention provides an isolated peptide having the amino acid sequence as set forth in SEQ ID NO: 2 (LSGDHC).

In some embodiments, a peptide of the present invention is capable of binding SOD1. In another embodiment, a peptide of the present invention is capable of binding mutant SOD1. In another embodiment, a peptide of the present invention is capable of binding only mutant SOD1 and not the wild-type (WT) SOD1.

In some embodiments, a peptide of the present invention is capable of preventing or reducing the generation of amyloid-like aggregates of misfolded SOD1. The term "amyloid-like aggregates" refers to insoluble highly structured protein aggregates. As a non-limiting example, amyloid-like aggregates typically bind and increase the fluorescence of the thioflavin T fluorescence probe. Amyloid-like aggregates or low-molecular weight intermediates formed in the course of amyloid-like aggregation have been suggested to be noxious species that cause ALS and/or effect the progression of ALS. While the exact nature (identity) of the toxic species formed in the course amyloid-like aggregation is unknown, amyloid-like aggregates are characterized by a fibril-like appearance of varied width or by a spherical or annular (pore-like) appearance characteristic of oligomeric protofibrillar aggregates similar to that of Aβ and α-synuclein.

The present invention also discloses peptides that are derived from hSOD1 that do not have the capability to prevent amyloid-like aggregate formation of misfolded SOD1. Such peptides may promote the formation of other type of aggregates and physical forms such as amorphous aggregates of irregular r shape and various size. In some embodiments, peptides that do not have the capability to prevent amyloid-like aggregate formation in the presence of misfolded SOD1 include, but are not limited to peptides having the amino acid sequence set forth in SEQ ID NO: 8, SEQ ID NO: 9, SEQ ID NO: 10, SEQ ID NO: 11 as described in example 3.

The terms "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "isolated" peptide refers to a peptide that is essentially free from contaminating cellular components, such as carbohydrate, lipid, or other proteinaceous impurities associated with the peptide in nature. Typically, a preparation of isolated peptide contains the peptide in a highly purified form, i.e., at least about 80% pure, at least about 90% pure, at least about 95% pure, greater than 95% pure, or greater than 99% pure.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D). Conservative substitution tables providing functionally similar amino acids are well known in the art.

The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, Proteins, 1984).

The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

The phrase "conservative substitution" also includes the use of a chemically derivatized residue in place of a non-derivatized residue provided that such peptide displays the requisite function of reducing the generation of amyloid-like aggregates of misfolded SOD1, as specified herein.

The term "derived from" or "corresponding to" refers to construction of a peptide based on the knowledge of a sequence using any one of the suitable means known to one skilled in the art, e.g. chemical synthesis in accordance with standard protocols in the art. A peptide derived from, or corresponding to human DOS1 (hSOD1; e.g., accession number NP000445), can be an analog, fragment, conjugate or derivative of a native amino acid human SOD1, and salts thereof, as long as said peptide retains its ability to bind SOD1.

Typically, the present invention encompasses derivatives of the peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —CH2-NH—, —CH2-S—, —CH2-S=0, OC—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C—O-0-C(R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxy amino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (MeAla), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide analogs, which can contain one or more D-isomer forms of the amino acids. Production of retro-inverso D-amino acid peptides where at least one amino acid, and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of, for instance, binding SOD1 or inhibiting aggregation of misfolded SOD1 as specified herein.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptides of the invention may be synthesized or prepared by techniques well known in the art. The peptides can be synthesized by a solid phase peptide synthesis method of Merrifield (see J. Am. Chem. Soc, 85:2149, 1964). Alternatively, the peptides of the present invention can be synthesized using standard solution methods well known in the art (see, for example, Bodanszky, M., Principles of Peptide Synthesis, Springer-Verlag, 1984) or by any other method known in the art for peptide synthesis.

In general, these methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha, alpha)-dimethyl-3, 5 dimethoxybenzyloxycarbonyl, o-nitrophenylsulfenyl, 2-cyano-t-butyloxycarbonyl, 9-fluorenylmethyloxycarbonyl (FMOC) and the like.

In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

The peptides of the invention may alternatively be synthesized such that one or more of the bonds, which link the amino acid residues of the peptides are non-peptide bonds. These alternative non-peptide bonds include, but are not limited to, imino, ester, hydrazide, semicarbazide, and azo bonds, which can be formed by reactions well known to skilled in the art.

The peptides of the present invention, analogs or derivatives thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

Included within the scope of the invention are peptide conjugates comprising the peptides of the present invention derivatives, or analogs thereof joined at their amino or carboxy-terminus or at one of the side chains, such as via a peptide bond to an amino acid sequence corresponding to or derived from a different protein. Additionally or alternatively, the peptides of the present invention, derivatives, or analogs thereof can be joined to another moiety such as, for example, a fatty acid, a sugar moiety, and a nucleic acid. Additionally or alternatively, the peptides of the present invention, derivatives, or analogs thereof can be joined to a tagging moiety such as, for example, a fluorophore, a chromophore, a chemilluminescent molecule, a magnetic particle, a dye or a radioactive isotope.

Conjugates comprising peptides of the invention and a protein can be made by protein synthesis, e. g., by use of a peptide synthesizer, or by ligating the appropriate nucleic acid sequences encoding the desired amino acid sequences to each other by methods known in the art, in the proper coding frame, and expressing the conjugate by methods commonly known in the art.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

In some embodiments, the isolated polypeptide of the present invention further comprises a cell-penetrating moiety. In some embodiments, the cell-penetrating moiety is a cell-penetrating peptide (CPP). In some embodiments, said CPP is linked to the N-terminus or C-terminus of the polypeptide of the invention. In some embodiments, said polypeptide of the invention and said CPP are linked by a covalent bond. In some embodiments, said polypeptide of the invention and said CPP are linked by a peptide bond. In some embodiments, said polypeptide of the invention and said CPP are linked by a non-covalent bond.

One skilled in the art is capable of selecting and deterring the CPP which may be used under the methods and compositions described herein. As a non-limiting example, the CPP may be selected from the peptides described in Siegmund Reissmanna, 2015, J. Pept. Sci. 2014; 20: 760-784, incorporate herein by reference in its entirety.

Antibodies

The term "antibody" (also referred to as an "immunoglobulin") is used in the broadest sense and specifically encompasses monoclonal antibodies and antibody fragments so long as they exhibit the desired biological activity.

According to another embodiment, the peptide of the present invention is an antigen. The term "antigen" as used herein refers to a peptide which is capable of causing production of antibodies that have the ability to bind to said peptide. In some embodiments, a peptide of the present invention is an antigen is used for production of monoclonal antibodies by methods well-known in the art.

In some embodiments, the antigen is a peptide comprising the amino acid sequence as set forth in SEQ ID NO: 2. In another embodiment, the antigen is a peptide comprising the amino acid sequence as set forth in SEQ ID NO:5. In another embodiment, the antigen is a peptide comprising at least 80%, at least 90%, at least, 95%, at least 98% homology to the amino acid sequence as set forth in SEQ ID NO: 5. In another embodiment, the antigen is a peptide having the amino acid sequence as set forth in SEQ ID NO: 11.

In some embodiments, a peptide of the present invention is an antigen used for production of antibodies by introduction of the peptide to a host. In some embodiments, the host is an animal such as, but not limited to: a rat, a mouse, a rabbit, a horse or a donkey. In some embodiments, the host is a human subject.

In some embodiments, the antibodies are isolated form the host and purified. In other embodiments, the antigen is used for eliciting an immune response in a subject in need thereof.

In some embodiments, the antigen is introduced to a host with a pharmaceutically acceptable carrier. In another embodiment, the antigen is introduced to a host with a pharmaceutically acceptable carrier further comprising an adjuvant. The term "adjuvant" as used herein refers to compounds that, when used in combination with specific vaccine antigens in formulations, augment or otherwise alter or modify the resultant immune responses. An adjuvant combined with a vaccine antigen increases the immune response to the vaccine antigen over that induced by the vaccine antigen alone. An adjuvant may augment humoral immune responses or cell-mediated immune responses or both humoral and cell-mediated immune responses against vaccine antigens.

In some embodiments, an antibody produced by using an antigen of the present invention is capable of binding the antigen. In another embodiment, an antibody produced by using an antigen of the present invention is capable of binding SOD1.

In another embodiment, administering an antibody of the present invention to a subject prevents the formation of amyloid-like SOD1 aggregates thereby treating the subject in need thereof.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed antibodies to be used in accordance with the methods provided herein may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, The monoclonal antibodies of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLONAL ANTIBODIES AND CANCER THERAPY, Alan R. Liss, Inc. (1985).

Besides the conventional method of raising antibodies in-vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

Pharmaceutical Compositions

In some embodiments, there is provided a pharmaceutical composition comprising as an active ingredient a therapeutically effective amount of a peptide of the present invention, and a pharmaceutically acceptable carrier or diluents.

The pharmaceutical compositions of the invention can be formulated in the form of a pharmaceutically acceptable salt of the peptides of the present invention or their analogs, or derivatives thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans.

The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the peptide of the invention, preferably in a substantially purified form, together with a suitable amount of carrier so as to provide the form for proper administration to the subject.

An embodiment of the invention relates to a peptide presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the location of the tissue of interest, the peptides of the present invention can be supplied in any manner suitable for the provision of the peptide to cells within the tissue of interest. Thus, for example, a composition containing the peptides of the present invention can be introduced, for example, into the systemic circulation, which will distribute said peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

In an embodiment of the invention, peptides are administered via oral, rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

The compositions of the present invention are generally administered in the form of a pharmaceutical composition comprising at least one of the active components of this invention together with a pharmaceutically acceptable carrier or diluent. Thus, the compositions of this invention can be administered either individually or together in any conventional oral, parenteral or transdermal dosage form.

Pharmaceutical compositions according to embodiments of the invention may contain 0.1%-95% of the active components(s) of this invention, preferably 1%-70%. In any event, the composition or formulation to be administered may contain a quantity of active components according to embodiments of the invention in an amount effective to treat the condition or disease of the subject being treated.

The peptides of the present invention, derivatives, or analogs thereof can be delivered in a controlled release system. Thus, an infusion pump can be used to administer the peptide such as the one that is used, for example, for delivering insulin or chemotherapy to specific organs or tumors. In one embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

Therapeutic Methods

In another embodiment, the present invention provides a method of treating, delaying the onset, delaying progression of, reducing the incidence of or reducing the severity of ALS in a subject, said method comprising administering to a subject a pharmaceutical composition of the present invention, thereby treating a subject afflicted with ALS.

In some embodiments, the term "treatment" as used herein refers to any response to, or anticipation of ALS and includes but is not limited to: preventing the ALS from occurring in a subject, which may or may not be predisposed to the condition, but has not yet been diagnosed with ALS and accordingly, the treatment constitutes prophylactic treatment for ALS; inhibiting ALS, e.g., arresting, slowing or delaying the onset, development or progression of the ALS; or relieving ALS, e.g., causing regression of the ALS or reducing the symptoms of ALS.

In another embodiment, the term "administering" as used herein, includes delivery of effective amounts of the composition of the present invention to a subject in need thereof. Methods for delivery of peptides are well known in the art.

In order to treat a patient, a therapeutically effective dose of the pharmaceutical composition of the present invention is administered. By "therapeutically effective dose" herein is meant a dose that produces the effects for which it is administered. The exact dose will depend on the purpose of the treatment, and will be ascertainable by one skilled in the art using known techniques. In some embodiments, dosages may range from 0.01 to 1000 mg/kg of subject body weight per day. In some embodiments, dosages may range from 0.1 to 50 mg/kg of subject body weight per day. In some embodiments, dosages may range from 1 to 100 mg/kg of subject body weight per day. In some embodiments, dosages may range from 1 to 500 mg/kg of subject body weight per day. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

In another embodiment, a peptide of the present invention is the only therapeutically active agent administered to a patient. Alternatively, the peptide is administered in combination with one or more other therapeutic agents affective for the treatment of ALS, including but not limited to Riluzole. Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Materials and Methods

Preparation of Structures.

For SMD analysis, equilibrated structures of SOD1 monomers extracted from the crystal structures of SOD1 dimers were used: PDB: 1HL5 for the WT. holo-SOD1 homo-dimer and PDB: 2GBU for the apo-SOD1 homo-dimer (C6A/C111A/C57A/C146A, lacking any disulfide bond forming potential). To model the presence of coordinated metals in the structure of holo-SOD1, the distances among the Cu' [H46 (ND1), H48(NE2), H63(NE2) and H120(NE2)] and $Zn^{2+}$ [H63 (ND1), H71 (ND1), H80 (ND1) and D83 (OD1)] ligands were restrained in all simulations by applying extra bonded terms in the form of a harmonic energy potential $U(x)=k\ (x-x_{ref})^2$, with the spring constant $k=50.0$ kcal/mol/$Å^2$. The SOD1 monomer structures were solvated in a water box [50×54×54 $Å^3$ (13,044 atoms in total) for the holo-SOD1 and 57×49×54 $Å^3$ (13,639 atoms in total) for the apo-SOD1] using $Ne/Cl^-$ for charge neutralization, minimized and equilibrated by using a molecular dynamics simulation with spatial constraints applied first to the whole protein (200 ps, water equilibration), then to the backbone atoms (100 ps) and finally without any spatial constraints, except for the distance constraints imitating the metals presence in the holo-SOD1 (100 ps), time sufficient to equilibrate the system as revealed by the NAIVID energy profile and RMSD variance of the protein atoms in trajectory. These and subsequent simulations were conducted in a isothermal-isobaric (NPT) ensemble at 310 K by using the NAMD program (version 2.9) and the CHARMM27 force field for proteins.

Steered Molecular Dynamics Simulation.

A list of surface-exposed residues in the equilibrated structures of the SOD1 monomers was generated as described elsewhere (R. Osman, M. Mezei, S. Engel., J. Comput. Chem. 2015, DOI: 10.1002/jcc.24276). The numbers of surface-exposed residues used in the SMD simulations were 95 and 97 for the holo-SOD1 and apo-SOD1, respectively. The SMD simulation was conducted for each surface residue without energy minimization by using the Cα atom as the SMD atom using the following scheme: the dummy atom was pulled at a constant velocity (0.15 Å/ps) in the direction of the vector connecting the Cα atom with the Cβ atom of a surface residue (in most cases, a direction approximating a normal to the local surface). During the simulation, no spatial constraints were applied to atoms within 15 Å of the SMD atom, whereas the Cα atoms outside the resulting 15 Å unconstrained hemisphere were set fixed. For each surface residue, the SMD simulation was repeated 12 times; applied forces were calculated from the SMD trajectories and plotted versus distances traveled by the dummy atoms. The plots were analyzed using a linear regression (Prism 6, GraphPad Software, Inc.), and the calculated slopes were referred to as the resistance coefficients (RC). The SOD1 dimer interface was delineated using the KFC (Knowledge-based FADE and Contacts) server. Structures were visualized and images were generated by using the VIVID software.

Purification and Evaluation of Recombinant $SOD1^{WT}$ and $SOD1^{G93A}$ Proteins.

Sequences of human $SOD1^{WT}$ and $SOD1^{G93A}$ were optimized for codon usage in E. coli, cloned into pHIS1 vector and expressed as 6His-tagged (N-term) soluble proteins in BL21 cells. Cells were grown in LB medium containing 100 µg/ml ampicillin at 30° C. for 4 h and the expression of the recombinant SOD1 proteins was induced by addition of 0.1 mM IPTG, followed by overnight incubation at 20° C. Cells were harvested by 25 min centrifugation (4,000×g) at 4° C. After 30 min incubation at ice, the cells were disrupted by sonication in a loading buffer (50 mM Ne/Phosphate, pH 7.6, 0.5 M NaCl, 2 mM β-mercaptoethanol, 10 mM imidazole) containing 1 mg/ml lysozyme and a protease inhibitor cocktail (Sigma, Israel). To remove DNA, the crude extract was incubated at ice for 30 min in the presence of 100 U/ml bovine pancreas DNaseI (Sigma, Israel) and 5 mM MgSO4, followed by 30 min centrifugation (20,000×g) at 4° C. The supernatant was loaded on a 5-ml HisTrap FF column (GE Healthcare Life Sciences, Sweden) equilibrated with the loading buffer. The column was washed with five column volumes (CV) of a washing buffer (50 mM Ne/phosphate, pH 7.6, 0.5 M NaCl, 2 mM β-mercaptoethanol, 20 mM imidazole) and the protein was eluted by a linear 20-400 mM imidazole gradient (10 CV). The peak fractions were dialyzed overnight at 4° C. against a storage buffer (50 mM Na/Phosphate, pH 7.6, 0.1 M NaCl, 2 mM β-mercaptoethanol and 10% glycerol), concentrated by ultrafiltration (10 kDa cutoff, Millipore, USA), centrifuged at 110,000×g at 4° C. for 1 h using ultracentrifuge (Sorvall M120, Discovery), and stored at −20° C. until use. Protein concentration was measured by the Bradford method using bovine serum albumin as standard.

The enzymatic activities of SOD1$^{WT}$ and SOD1$^{G93A}$ were assessed by an in-gel activity assay. Protein samples (20 μg) were separated on a 10% native polyacrylamide gel. The gel was stained in a dark environment using a solution containing 0.3 mM riboflavin, 0.3 mM Nitro Blue Tetrazolium (NBT) and 1% TEMED and kept under a white light for 30 min at r.t.

For size exclusion chromatography, purified SOD1$^{WT}$ and SOD1$^{G93A}$ were incubated at 37° C. in 50 mM Na$^+$/phosphate buffer, pH 7.6, containing 0.1 M NaCl, 1 mM EDTA, and 1 mM TCEP for the indicated time and separated on Superdex 200 10/300 GL column (GE Healthcare Life Sciences, Sweden) at flow rate of 0.5 ml/min using 50 mM Ne/phosphate, pH 7.6, 0.1 M NaCl as running buffer.

Peptide Binding to SOD1.

Peptides were synthesized by GL Biochem Ltd. (Shanghai, China). Peptide identity and purity (>90%) was confirmed by MS and HPLC analyses. For microscale thermophoresis (MST) analysis, the proteins (SOD1$^{WT}$ and SOD1$^{G93A}$) were labeled with BLUE fluorescent dye NT-495-NHS (lysine chemistry) using a Monolith NT protein labeling kit Blue-NETS (Nano Temper Technologies, Munchen, Germany) at a protein (monomer):dye ratio of 1:3 as recommended by the manufacturer.

The assessment of peptide binding to the proteins was carried out using Monolith NT.115 (NanoTemper Technologies, Munchen, Germany). The labeled SOD1$^{WT}$ (200 nM) or SOD1$^{G93}$A (300 nM) was incubated for 1.5 h in 50 mM Ne/phosphate binding buffer, pH 7.6, 0.1 M NaCl, 0.1 mM TCEP, 0.04% Tween-20 and 1 mg/ml BSA at r.t. with increasing concentrations of peptide (0-100 μM) dissolved in DMSO or DMF (if the peptide contained cysteine residues). The final concentration of either DMSO or DMF in the binding buffer was 1%. The SD-denaturation test, in which samples were incubated for 5 min at 95° C. in the presence of 4% SDS and 40 mM DTT, was performed according to the manufacturer's instructions. The binding data were analyzed by a non-linear regression using a logistic (three parameter) function implemented in Prism6 (GraphPad) program.

ThT Aggregation Assay for SOD1 and SDD1-Derived Peptides.

Prior to the aggregation assay, all mixtures containing protein and/or peptide were filtered through a 0.22 μm Millex-GV (PVDF) syringe filter, 4 mm (Millipore, USA). SOD1$^{G93A}$ (50 μM) or peptide (600 μM) were incubated in 200 μl of 20 mM Ne/phosphate buffer, pH 7.0, 0.1 M NaCl, 5 mM EDTA, 1 mM TCEP, and 1% DMF in the presence of 50 μM Thioflavin T (Sigma Aldrich, Israel) in a black 96-well plate at 37° C. with continuous shaking (set to fast) using a SpectraMax Paradigm (Molecular Devices) ELISA reader. The fluorescence (Exc. 440 nm; Em. 485 nm) was measured at 5 min intervals.

Analysis of SOD1 Fibril Formation by Transmission Electron Microscopy (TEM).

Samples for TEM imaging were prepared as follows: at the end of the aggregation assay, 2.5 μl samples (diluted 5-fold) were deposited on a carbon-coated copper 300 mesh. After 1 min, the excess liquid was carefully blotted by a filter paper. Followed 1 min drying at the ambient temperature, 5 μl of 2% uranyl acetate was added. After 1 min, the excess of the salt solution was carefully removed with a filter paper. The imaging was performed using a Tecnai G2 12 BioTWIN (FEI) transmission electron microscope with an acceleration voltage of 120 kV. Depending on the aggregate size, different magnifications were used. The visible features were sensitive to the electron beam exposure, indicating their organic origin.

Immunoprecipitation (IP) Analysis of SOD1 Misfolding.

Purified recombinant SOD1$^{G93A}$ or SOD1$^{WT}$ proteins (50 mM) were incubated for 4 h in 50 mM Tris-HCl buffer, pH 7.4, 150 mM NaCl, 1 mM EDTA, in the presence or absence of peptide SE-12 (SEQ ID NO: 7) (600 μM) at 4 or 37° C. After incubation, 10 μg of SOD1 proteins were transferred into immunoprecipitation (IP) buffer (50 mM Tris-HCl, pH 7.4, 150 mM NaCl, 1 mM EDTA, and 0.5% Nonidet P-40 plus protease inhibitors) and incubated at 4° C. overnight with B8H10 monoclonal antibody (MediMabs) crosslinked to protein G beads (Dynabeads, Invitogen) using dimethyl pimelimidate (Pierce) according to the manufacturer's instructions. The beads were magnetically isolated and washed three times with IP buffer. Samples were eluted by boiling in 2× sample buffer. Both bound and unbound IP fractions were then separated by SDS-PAGE, transferred to a nitrocellulose membrane and probed with goat anti-SOD1 antibody (C-17; Santa Cruz Biotechnology).

Example 1

Misfolding Alters the Surface Backbone Dynamic Properties of SOD1

SMD analysis was used to compare the dynamic properties of the surface backbone of the monomers of human WT holo-SOD1 and of reduced demetallated apo-SOD1 (C6A/C111A/C57A/C146A, lacking any disulfide bond-forming potential). Based on the assumption that apo-SOD1 species (either WT or mutant) represent a misfolded (or partially misfolded) form of SOD1 responsible for aberrant activities, such an analysis was expected to provide new insight into the molecular basis of the noxious gain-of-function of misfolded SOD1.

The analysis revealed that the holo-SOD1 surface backbone, in which 53% of surface-exposed residues have a static character, was exceptionally rigid. These static residues constituted a number of extended stability patches, the largest of which was situated at the dimer interface and comprised the amino acids shaded in grey in FIG. 1A.

Example 2

SOD1 Stability Patch-Derived Derived Peptides Bind SOD1

Figure 2A:
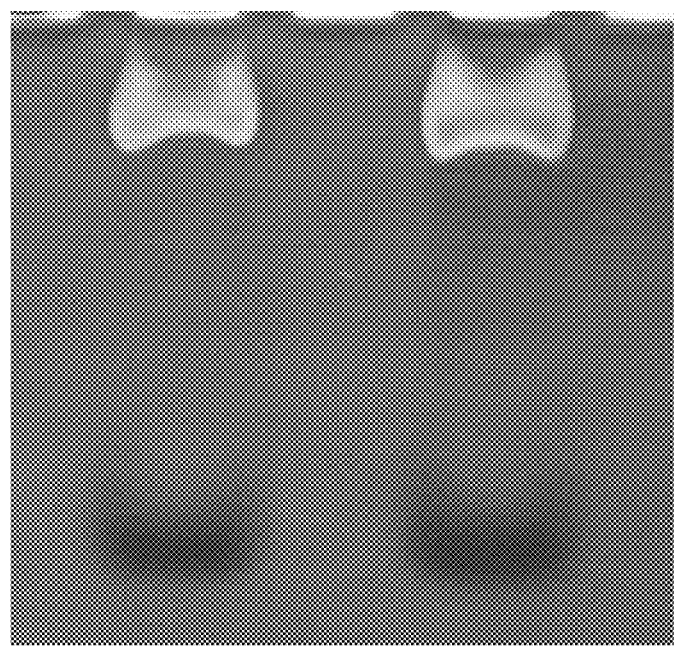
FIGS. 2A-2B show results of the analysis of properties of recombinant SOD1$^{WT}$ and SOD1G93A.
Figure 2B:
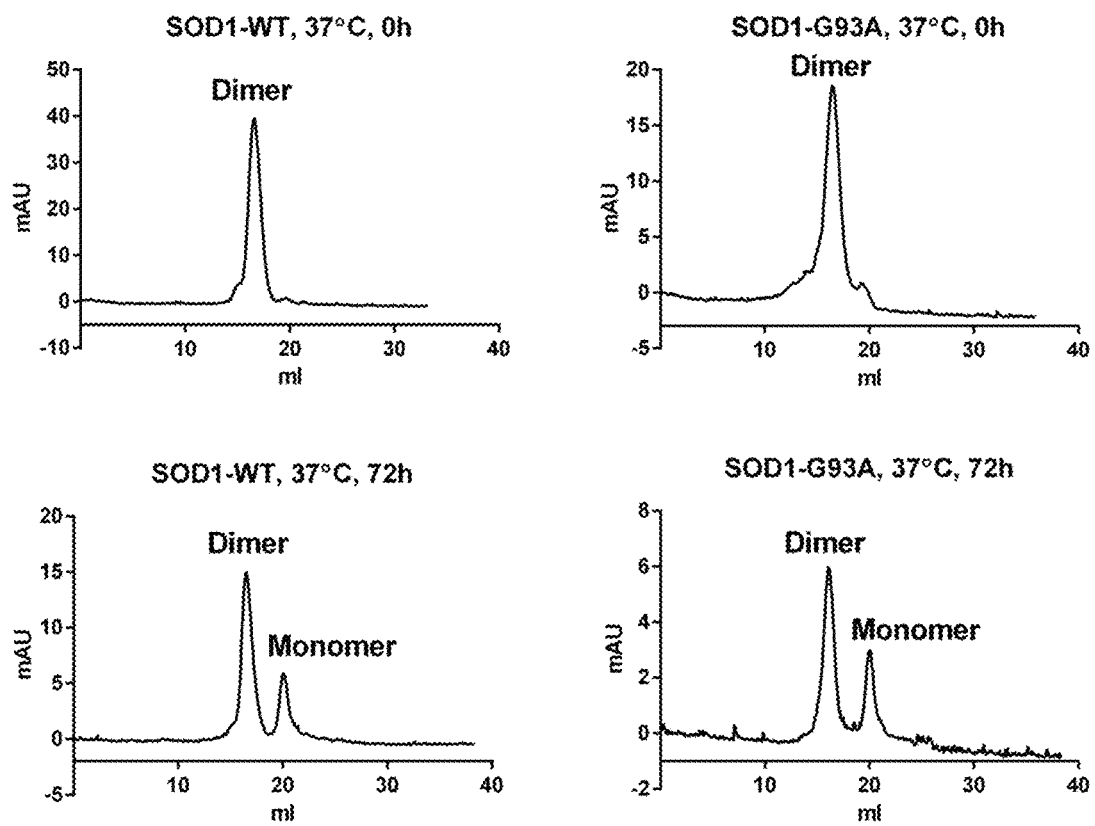

Fourteen 20-mer peptides derived from the stability patch of apo-SOD1 were synthesized (FIGS. 1A-B) and tested their ability to bind SOD1 proteins. In cells, SOD1$^{WT}$ co-expressed with a FALS mutant aggravates pathological conditions, potentially by interacting with and prolonging the life-time of a soluble mutant form. In addition, misfolded SOD1 may be capable of propagating intercellular pathology in a prion-like manner by inducing noxious misfolding in structurally intact SOD1. Thus, both mutant and SOD1$^{WT}$ are expected to interact with misfolded SOD1. For functional assays, recombinant proteins of SOD1$^{WT}$ and a clinically relevant SOD1$^{G93A}$ mutant were used. These proteins were expressed in *E. coli* and purified under non-denaturing conditions in an enzymatically active form (FIGS. 2A-B). According to the gel-filtration analysis, SOD1$^{WT}$ and SOD1$^{G93A}$ were dimers that partially monomerized upon prolonged incubation at 37° C., during which SOD1$^{WT}$ remained fully soluble and SOD1$^{G93A}$ partially precipitated (FIG. 2B). Recombinant SOD1 produced in an *E. coli* host appears to constitute a particularly appropriate target (without further treatment) for elucidating the molecular mechanism of SOD1 pathology in ALS. *E. coli* is ineffective in promoting disulfide bond formation and metal incorporation into SOD1. Thus, the resulting protein most probably exists in bacteria as a mixture of structural states at various stages of misfolding. This renders the recombinant SOD1 a close mimetic of endogenous SOD1, which exists under conditions of reduced turnover and environmental stresses known to promote misfolding and apo-SOD1 formation.

The binding of synthetic peptides to fluorescently labeled SOD1$^{WT}$ or SOD1$^{G93A}$ was assessed using a microscale thermophoresis technique (MST). Two overlapping peptides, designated SE-11 (SEQ ID NO: 6) (SOD1 aa. 90-109, DKDGVADVSIEDSVISLSGD) and SE-12 (SEQ ID NO: 7) (SOD1 aa. 106-125, LSGDHCIIGRTLVVHEKADD), inflicted a specific, dose-dependent increase in the fluorescence of the target proteins (FIGS. 3A-D). The increase in fluorescence was observed with both SOD1$^{WT}$ and SOD1$^{G93A}$ for SE-12 (SEQ ID NO: 7), while the effect was obtained only with SOD1$^{G93A}$ for SE-11 (SEQ ID NO: 6).

Example 3

SOD1 Stability Patch Derived Peptides Affect the Kinetics of SOD1 Amyloid Formation and the Morphology of the Formed Aggregates The effect of the binding of SOD1-derived peptides to misfolded SOD1 on kinetics of SOD1 aggregation was tested. The time course of SOD1$^{G93A}$ aggregation was followed by monitoring the fluorescence of a thioflavin T (ThT) probe. Over the course of incubation, SOD1$^{G93A}$ triggered a ThT response, and TEM imaging at the end of incubation revealed the formation of fibril-like 14-16 nm width fibrils along with small 0.1-0.2 μm diameter spherulites (FIGS. 3A-D and FIG. 4A [i-iii]).

Figure 3A:
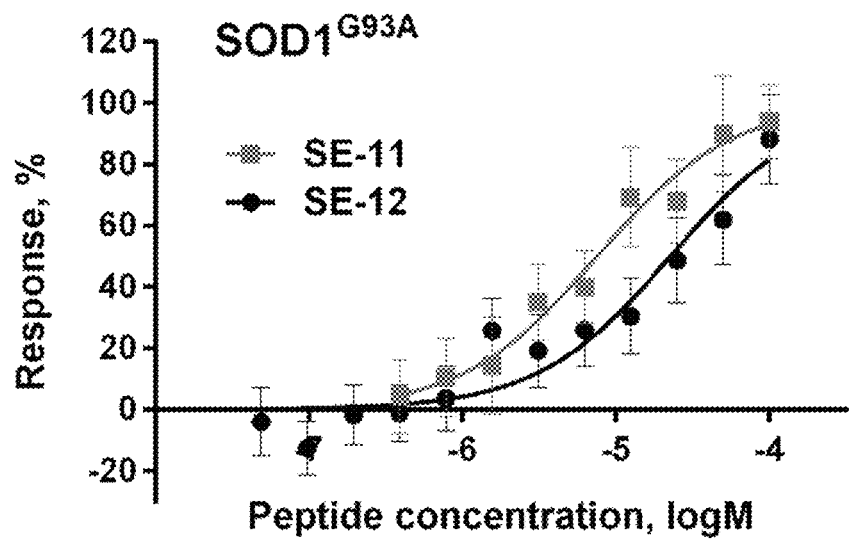
FIGS. 3A-3B are plots showing results of testing of the interaction of peptides SE-11 (SEQ ID NO: 6) and SE-12 (SEQ ID NO: 7) with SOD1. Fluorescently labeled recombinant SOD1G93A (300 nM) (FIG. 3A) or SOD1$^{WT}$ (200 nM) (FIG. 3B) were incubated for 1.5 h at r.t. with increasing concentrations of a peptide, and the fluorescence was measured using an MST instrument (NanoTemper). The changes in SOD1$^{WT}$ fluorescence in the presence of SE-11 (SEQ ID NO: 6) were not plotted because of a low signal to noise ratio. The effects of both peptides on SOD1 fluorescence were abolished by protein denaturation (SD-denaturation test), indicating that specific interaction with the peptide caused the observed changes in the SOD1 fluorescence. The curves represent the non-linear regression analyses of the data using a logistic (three parameters) function. The results are expressed as the mean±S.D. of at least three independent experiments.
Figure 3B:
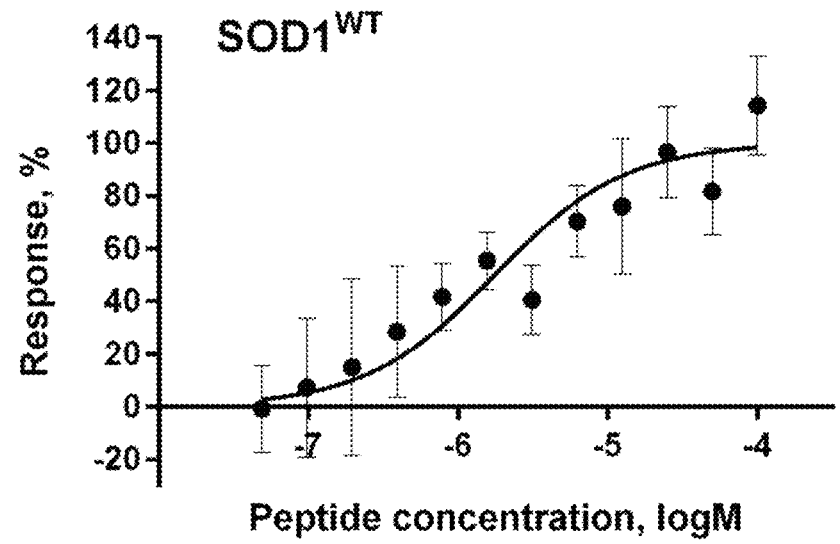
Figure 3C:
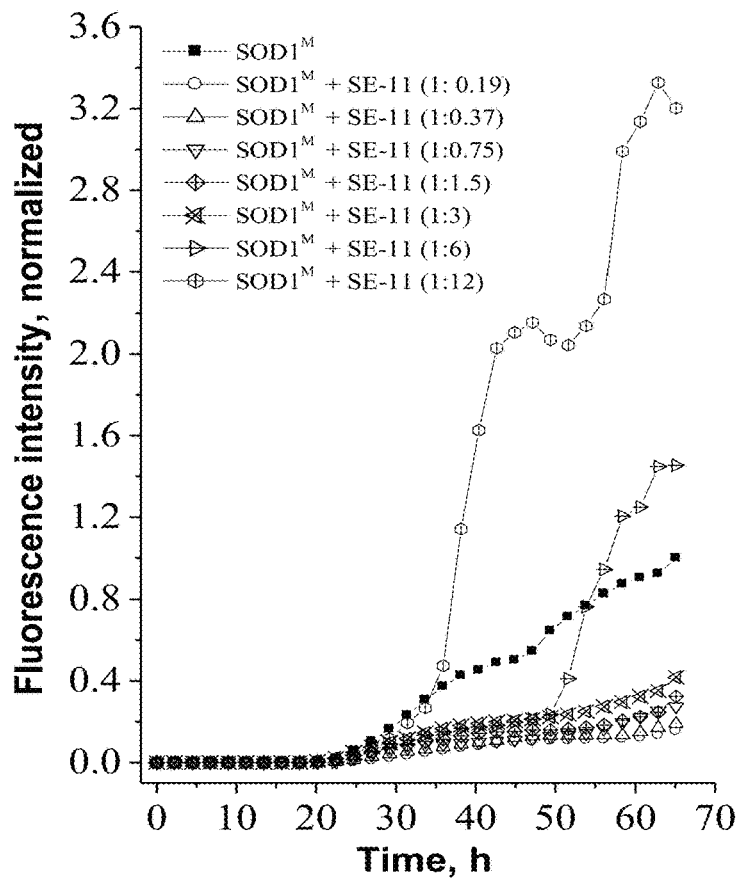
FIGS. 3C-3D are plots showing test results of the effect of peptides SE-11 (SEQ ID NO: 6) and SE-12 (SEQ ID NO: 7) on the kinetics of SOD1G93A amyloid formation. ThT fluorescence was monitored in the course of SOD1G93A (50 mM) co-incubation with SE-11 (SEQ ID NO: 6) (FIG. 3C) or SE-12 (SEQ ID NO: 7) (FIG. 3C) at different molar ratios at 37° C. with continuous shaking. SOD1M designates SOD1G93A. The values were normalized to the maximal ThT intensity elicited by SOD1G93A alone. All results are expressed as an average of assays performed in triplicate in a representative experiment.
Figure 3D:
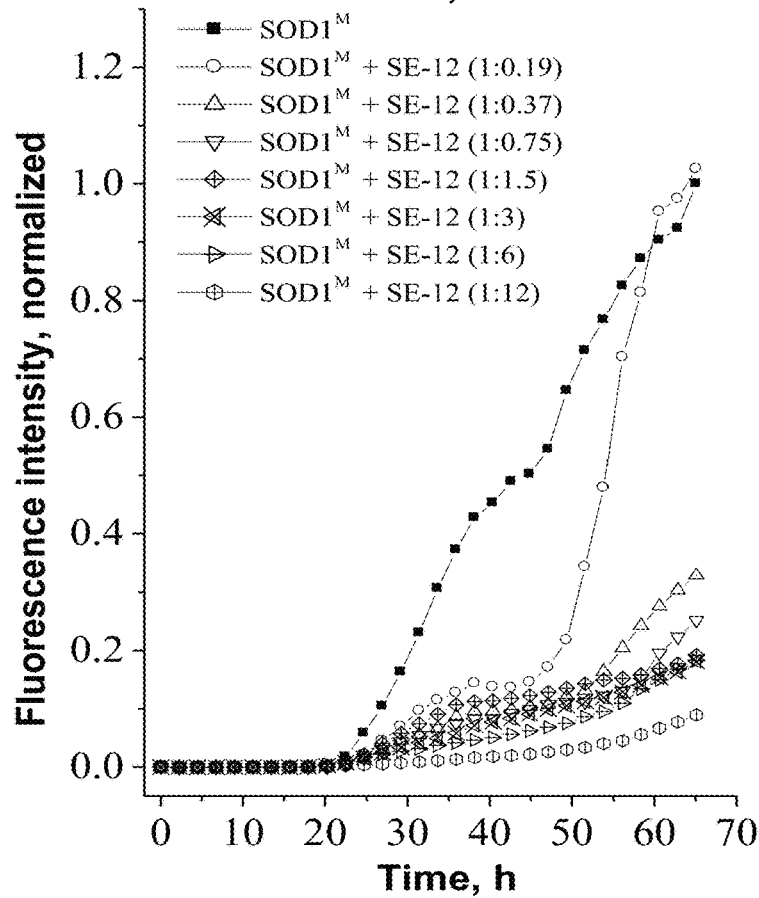
Figure 4A:
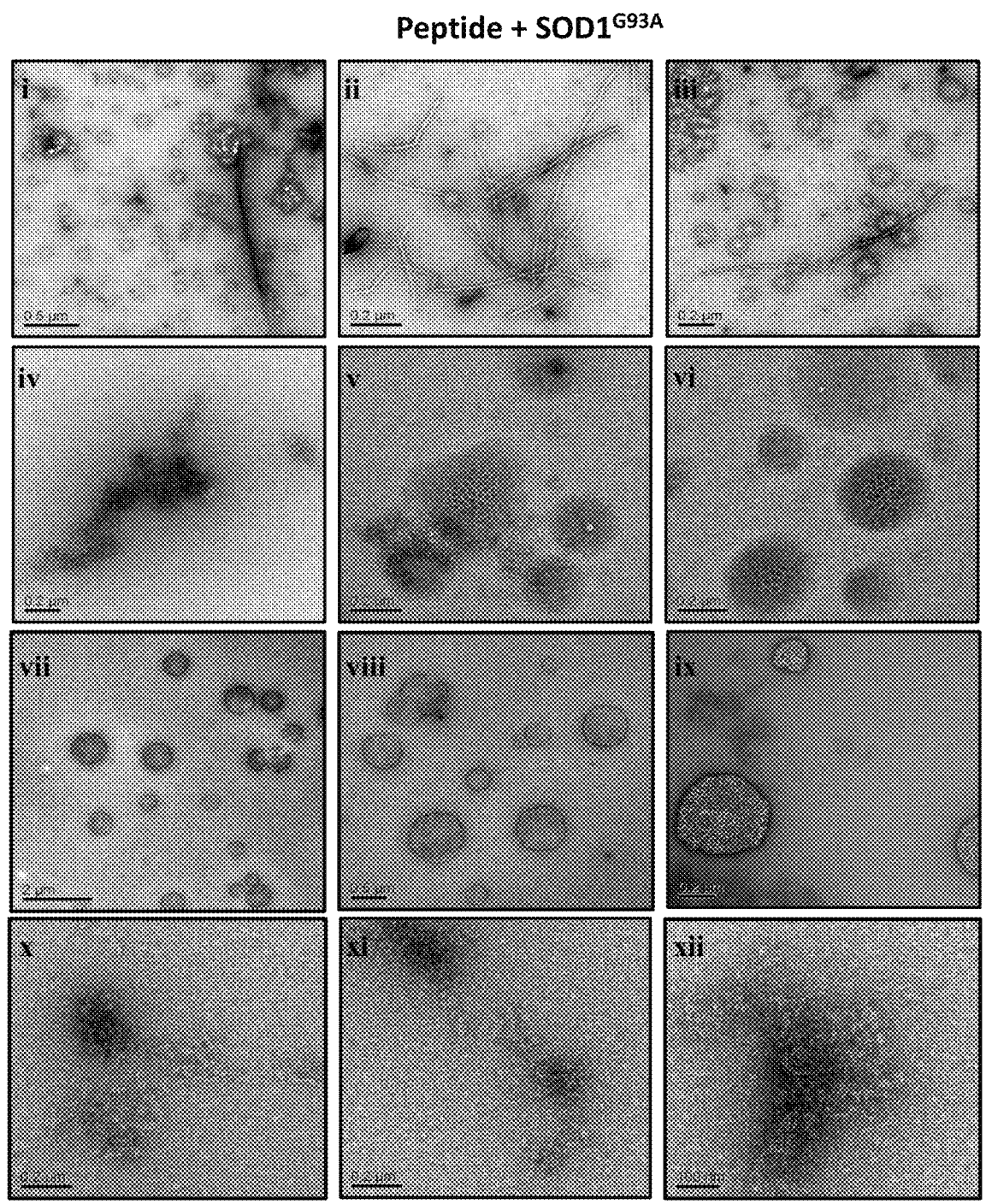
FIGS. 4A-4B are exemplary transmission electron microscopy (TEM) images showing the effect of peptides on the morphology of SOD1$^{G93A}$ aggregates.

At low peptide:SOD1 molar ratios, SE-11 (SEQ ID NO: 6) peptide inhibited the ThT response of SOD1$^{G93A}$ and suppressed the formation of characteristic fibril-like aggregates, but some amorphous aggregates and spherulites of irregular shape and various size were detected by TEM (FIG. 3C and FIG. 4A [iv-vi]). The inhibitory effect of SE-11 (SEQ ID NO: 6) was reversed with increased SE-11 (SEQ ID NO: 6) concentrations, resulting in a significantly enhanced ThT response compared to SOD1$^{G93A}$ alone at peptide: SOD1 molar ratios higher than 3 (FIG. 3C and FIG. 4A [vii-ix]). Under these conditions, TEM mainly detected the presence of large spherulites (0.5-1.0 μm diameter), which may be accountable for the higher ThT response obtained at this molar ratio. In contrast, SE-12 (SEQ ID NO: 7) peptide inhibited the SOD1$^{G93}$A-triggered ThT response and fibril formation in a dose-dependent manner (FIG. 3D and FIG. 4A [x-xii]), although amorphous aggregates were detected by TEM at the end of the incubation. The formation of amyloid-like ThT-responsive aggregates of SOD1$^{G93A}$ and SE-12 (SEQ ID NO: 7) was mutually inhibited in mixtures (FIG. 4A [x-xii]).

Co-incubation of peptides SE-19 (SEQ ID NO: 9) and SE-20 (SEQ ID NO: 10) with SOD1$^{G93A}$ resulted in the formation of amyloid-like (ThT-responsive) aggregates whose morphology was different from that of the aggregates obtained with SOD1$^{G93A}$ alone (FIG. 4a [i-iii]).

Figure 4B:
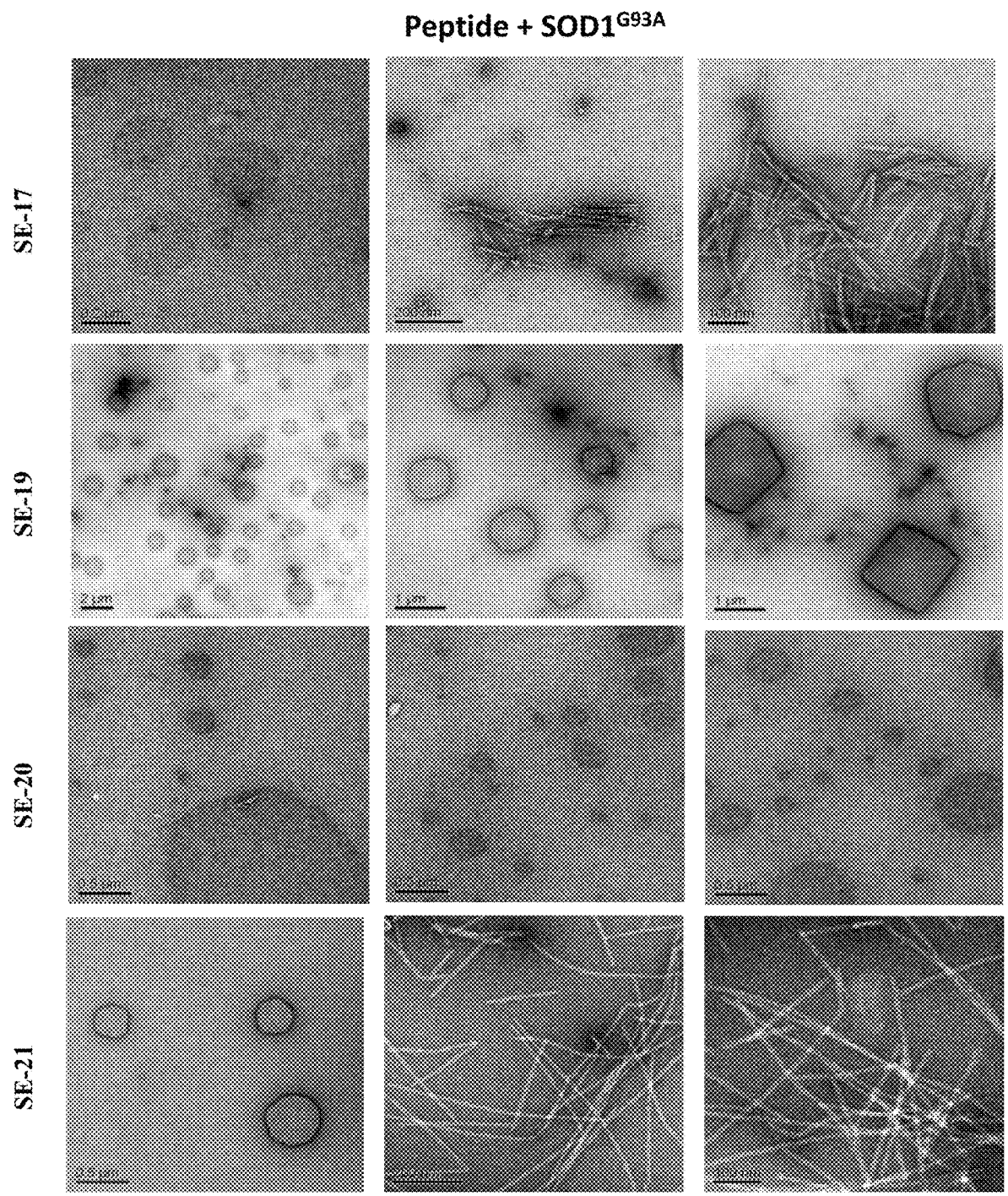

Co-incubation of the peptides SE-17 (SEQ ID NO: 8) and SE-21 (SEQ ID NO: 11) with SOD1$^{G93A}$ did not prevent aggregation. As with peptides SE-19 (SEQ ID NO: 9) and SE-20 (SEQ ID NO: 10), the aggregates formed in the presence of SE-17 (SEQ ID NO: 8) and SE-21 (SEQ ID NO: 11) had different morphology (size) from that of the aggregates obtained with SOD1$^{G93A}$ alone (FIGS. 4B and 5)

Example 4

Sequence within SOD1 May Contribute Binding of Specific Forms of SOD1

To test the function of the exposed $^{106}$LSGDHC$^{111}$ epitope on misfolding of other SOD1 molecules, the effect of the SE-12 (SEQ ID NO: 7) peptide on SOD1 misfolding was tested using immunoprecipitation with a mAb (B8H10) that specifically recognizes misfolded SOD1. B8H10 antibody does not immunoprecipitate intact SOD1$^{WT}$ and can detect a wide variety of SOD1 mutants (Gros-Louis et al., 2010). As demonstrated in FIG. 6A-B, incubation of SOD1$^{WT}$ with the SE-12 (SEQ ID NO: 7) peptide significantly increased the amount of accumulated misfolded species. The effect of the peptide was more prominent at 4° C., when the intrinsic rate of SOD1$^{WT}$ misfolding is low, than at 37° C. Therefore, the interaction with SE-12 (SEQ ID NO: 7) destabilizes SOD1$^{WT}$ structure, imitating the destabilizing effect of temperature. The misfolding of SOD1$^{G93A}$ was affected by SE-12 (SEQ ID NO: 7) to a much smaller extent at both temperatures (FIGS. 6C-D). For SOD1$^{G93A}$, more misfolded protein was observed at 4° C. in the absence of the peptide compared to SOD1$^{WT}$, indicating that interaction with SE-12 (SEQ ID NO: 7) may mimic the effect of the G93A mutation on the SOD1 structure. These findings indicate that the interaction of the exposed $^{106}$LSGDHC$^{111}$ epitope in misfolded SOD1 with an intact SOD1$^{WT}$ dimer may contribute to the prion-like ability of misfolded SOD1 to propagate a noxious misfolding signal among structurally intact SOD1 molecules (either intra- or inter-cellularly).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An isolated polypeptide of less than 50 amino acids, said polypeptide comprises the amino acid sequence as set forth in SEQ ID NO: 2 (LSGDHC).

2. The isolated polypeptide of claim 1, wherein said polypeptide comprises the amino acid sequence as set forth in SEQ ID NO: 4 (LSGDHCX$_1$), wherein X$_1$ represents an amino acid sequence of 1 to 15 amino acid residues, contiguous thereto.

3. The isolated polypeptide of claim 1, wherein said polypeptide comprises the amino acid sequence as set forth in SEQ ID NO: 7 (LSGDHCIIGRTLVVHEKADD).

4. The isolated polypeptide of claim 1, wherein said polypeptide comprises an amino acid sequence having at least 95% homology to SEQ ID NO: 7.

5. The isolated polypeptide of claim 1, wherein said polypeptide comprises the amino acid sequence as set forth in SEQ ID NO: 5 (X$_2$LSGDHCX$_3$), wherein X$_2$ represents between 1 to 15 amino acid residues preceding thereto and X$_3$ represents between 1 to 15 amino acid residues contiguous thereto.

6. The isolated polypeptide of claim 1, wherein said polypeptide comprises the amino acid sequence as set forth in SEQ ID NO: 11 (EDSVISLSGDHCIIGRT).

7. The isolated polypeptide of claim 1, wherein said polypeptide comprises an amino acid sequence having at least 95% homology to SEQ ID NO: 11.

8. The polypeptide of claim 1, having a length of less than 40 amino acids.

9. The polypeptide of claim 1, further comprising a cell-penetrating moiety.

10. The polypeptide of claim 9, wherein said cell-penetrating moiety is a cell-penetrating peptide (CPP).

11. The polypeptide of claim 10, wherein said CPP is linked to the N-terminus or C-terminus of said polypeptide.

12. The polypeptide of claim 10, wherein said CPP is linked to said polypeptide by a peptide bond.

13. The isolated polypeptide of claim 1 for producing anti-SOD1 antibodies.

14. The isolated polypeptide of claim 13, wherein said antibodies are monoclonal antibodies.

15. A composition comprising the isolated polypeptide of claim 13 and an adjuvant.

16. The isolated polypeptide of claim 13, wherein said polypeptide comprises the amino acid sequence of SEQ ID NO: 2.

17. The isolated polypeptide of claim 13, wherein said polypeptide comprises the amino acid sequence of SEQ ID NO: 5.

18. The isolated polypeptide of claim 13, wherein said polypeptide comprises the amino acid sequence of SEQ ID NO: 11.

* * * * *